United States Patent [19]

Long

[11] 3,975,512
[45] Aug. 17, 1976

[54] NON-TOXIC BROMINATED PERFLUOROCARBONS RADIOPAQUE AGENTS

[75] Inventor: David M. Long, Jr., Villa Park, Ill.

[73] Assignee: University of Illinois Foundation, Urbana, Ill.

[22] Filed: Aug. 26, 1974

[21] Appl. No.: 500,463

Related U.S. Application Data

[63] Continuation of Ser. No. 100,408, Dec. 21, 1970, abandoned.

[52] U.S. Cl. ............................ 424/5; 252/312; 424/350
[51] Int. Cl.² ...................................... A61K 29/02
[58] Field of Search ............... 429/5; 260/653; 424/350; 252/312

[56] References Cited
UNITED STATES PATENTS

| | | | |
|---|---|---|---|
| 2,678,953 | 5/1954 | Conly | 260/653 |
| 3,055,953 | 9/1962 | Smeltz | 260/653.1 |
| 3,377,393 | 4/1968 | Yale | 260/653 |
| 3,381,042 | 4/1968 | Yale | 260/653 |
| 3,456,024 | 7/1969 | Loree | 260/653 |
| 3,499,089 | 3/1970 | Regan | 424/350 |

*Primary Examiner*—James O. Thomas, Jr.
*Assistant Examiner*—Vera C. Clarke
*Attorney, Agent, or Firm*—Merriam, Marshall, Shapiro & Klose

[57] ABSTRACT

Non-toxic bromofluorocarbon radiopaque agents are disclosed. Certain monobrominated acyclic fluorocarbons, e.g., $CF_3(CF_2)_6CF_2Br$, are improved non-toxic radiopaque agents useful in diagnostic roentgenology, for example in visualizing the gastrointestinal tract, the tracheobronchial tree, the alveolar spaces or parenchyma of the lung, the spleen, the urinary bladder and ureters, the common bile duct and its radicals, the pancreatic ducts, the blood vessels, etc.

13 Claims, No Drawings

NON-TOXIC BROMINATED PERFLUOROCARBONS RADIOPAQUE AGENTS

This is a continuation, application Ser. No. 100,408, filed Dec. 21, 1970, now abandoned.

My copending application, Ser. No. 100,293 filed Dec. 21, 1970, now U.S. Pat. No. 3,818,229, describes a new class of radiopaque agents comprising brominatd perfluorocarbons. As disclosed therein, monobromo, and dibromo perfluorocarbons, including both aliphatic and cyclic compounds, exhibit radiopaque properties which make such brominated perfluorocarbons useful, for example, in various industrial applications such as radiologic processes for examining materials, (e.g., plastics) and/or devices (e.g., pacemakers) to discover flaws or defects.

The present invention relates to non-toxic radiopaque agents. In general, it concerns the use of certain bromofluorocarbons as non-toxic radiopaque agents, in medical applications. More particularly, the present invention concerns improved radiopaque agents comprising certain monobrominated acyclic fluorocarbons, e.g., $CF_3(CF_2)_6CF_2Br$ and the use of such agents in medical applications.

The present invention is directed to and based, in part, upon the unexpected discovery that, monobrominated acyclic perfluorocarbons are essentially non-toxic, making such radiopaque agents, particularly suitable for medical applications involving animals, including humans.

As employed herein, the term "radiopaque agent" means a substance which functions as a contrast media permitting X-ray visualization of one or more desired parts of a material; the term "medical applications" refers to processes wherein one or more parts of the anatomy of an animal are contacted with a radiopaque agent; and the term "non-toxic" refers to a radiopaque agent which can be used, in medical applications, to contact one or more desired parts of the anatomy of an animal without producing toxic effects.

In general, an ideal radiopaque agent for use in medical applications should be capable of producing clear concise shadows of the desired part or parts of the anatomy. It should also be shelf-stable, easily administered, and rapidly carried to the desired location(s) in the body for contrast. Moreover, it should be retained in the desired part or parts of the anatomy for a period of time necessary for X-ray diagnosis or visualization and then excreted or eliminated rather rapidly without toxic effects.

In the prior art, barium sulfate has commonly been employed as a radiopaque agent for use in medical applications, particularly for roentgenologic examinations of the gastrointestinal tract in humans. In addition, soluble iodinated organic compounds, for example, sodium diatrizoate and meglumine diatrizoate, have also been used as radiopaque agents for urographic studies and the like. Certain fluoro-iodo benzene compounds have been considered as radiopaque agents and found to be rather irritating to the gastrointestinal tract, making such compounds unacceptable for use in the gastrointestinal tract.

The present invention provides radiopaque agents which exhibit improved radiodensity, are shelf-stable, easily administered, and eliminated, and are non-toxic. In one embodiment of the present invention, there is provided a radiopaque agent which is highly efficacious for roentgenologic examinations of the gastrointestinal tract.

Briefly, the improved radiopaque agents of the present invention comprise certain bromofluorocarbons. The bromofluorocarbons found suitable for use generally comprise monobrominated acyclic (aliphatic) perfluorocarbons. Preferably the radiopaque agents of the present invention will comprise perfluoroalkylbromides in which the alkyl group contains 6 to 8 carbon atoms. A particularly preferred radiopaque agent is perfluoroctylbromide, having the formula $CF_3(CF_2)_6CF_2Br$.

Bromofluorocarbons, including aliphatic monobromofluorocarbons, and their methods of manufacture are known and, per se, form no part of the present invention. Kirk-Othmer, *Encyclopedia of Chemical Technology*, vol. 9, p. 748–750, Second Edition, describes, for example, the manufacture of aliphatic bromofluorocarbons.

The radiopaque agents of the present invention are liquid materials at ambient temperatures and are generally in the liquid state when used. For example, the radiopaque agent can be used as a pure liquid without any other materials or can also be used as a solution or an emulsion or suspension in which small particles of the radiopaque agent are dissolved, suspended or dispersed in a non-toxic vehicle or carrier, for example, Ringer's solution.

Such solutions or emulsions may also contain minor amounts of other ingredients, such as: buffers, e.g., sodium citrate; sequestering agents, e.g., disodium edetate; chemotherapeutic agents, e.g., nitrogen mustard; antibiotics, e.g., tetracycline; and/or one or more emulsifying agents, for example, "Pluronic F-68."

Suitable aqueous emulsions have been employed wherein the radiopaque agent is present in a concentration of about 1 to about 12 parts by weight for each part of the aqueous phase present in the emulsion. The concentration, of course, affects the degree of radiodensity, as well as the viscosity of the radiopaque agent. when the concentration is less than about 0.5 part radiopaque agent insufficient radiodensity results, and when the concentration exceeds about 12 parts the aqueous emulsion becomes viscous to the extent that problems of preparation and/or administration occur.

In addition to being employed in the liquid form, i.e., as either a pure liquid (i.e., about 99.98 to 100% active ingedient), a solution, or an emulsion, the radiopaque agents of the present invention may also be employed in the form of an aerosol. In this latter embodiment, the normally liquid radiopaque agent is confined in a container, under pressure, with one or more suitable aerosol propellents. Suitable propellents are well known in the aerosol formulation art and include, for example, fluorinated hydrocarbons such as Propellents "11", "12", "114" and "318". One such aerosol formulation comprises about 20 wt.% $CF_3(CF_2)_6CF_2Br$, and about 80 wt.% of "Freon 12" (as the propellent).

The radiopaque agents of the present invention can be used or administered in medical applications according to procedures known in the art and used heretofore in administering prior art radiopaque agents. Thus, the radiopaque agents can be administered orally, rectally, intraperitoneally, subcutaneously, transracheally, intravascularly, via catheters in the urinary bladder and ureters, intrathecally and via catheters in the bile ducts or pancreatic ducts, etc. The choice of a particular method of administration will depend of course upon the part or parts of the anatomy to be visualized, as well as upon the medical history and current medical status of the subject receiving the radiopaque agent.

The amount or dosage of radiopaque agent to be employed in any specific instance will, of course, be determined by those skilled in the art, and is not, per se, a part of the invention. Generally, dosages on the order of about 1 to about 10 milliliters (of radiopaque agent) per kilogram (of body weight) (ml./kg.) are contemplated.

The present invention can be further understood by reference to the following illustrative examples.

EXAMPLE I

In this example a radiopaque agent of the present invention was compared with two a radiopaque commonly used prior art radiopaque agents, viz, oral barium sulfate and oral sodium diatrizoate [Hypaque].

The radiopaque agent of the invention comprised perfluoroctylbromide employed in the form of a liquid and administered orally to dogs at a dosage of about 8 to about 10 ml./kg.

Barium sulfate and sodium diatrizoate were separately orally administered to other dogs at commonly recommended dosages.

X-ray studies on the gastrointestinal tract were made and the resulting X-rays were reviewed for efficacy. The efficacy studies indicated that the perfluoroctylbromide provided superior visualization of the wall structures and fine details of the gastrointestinal tract.

In addition, perfluoroctylbromide proved unexpectedly superior to both oral barium sulfate and oral sodium diatrizoate in the following respects. The transit time, (i.e., the time necessary for the radiopaque agent to travel from the stomach to the rectum), of perfluoroctylbromide is substantially less. Thus, the use of the radiopaque agent of the present invention can result in a considerable savings in a patient's discomfort, time, and money since its use would permit gastrointestinal studies to be completed in a fraction of the time necessary for such studies using currently available prior art radiopaque agents. Moreover, the use of the perfluoroctylbromide did not result in diarrhea, whereas the use of sodium diatrizoate did cause diarrhea in the dogs.

These studies also indicated that the use of perfluoroctylbromide in an obstructed gastrointestinal tract did not result in caking, nor cause impaction. Further, perfluoroctylbromide produced a coating of excellent quality on the mucosa of the gastrointestinal tract, resulting in excellent detail of mucosa structure on X-ray films.

EXAMPLE II

In this example radiopaque agents of the present invention were compared to other brominated perfluorocarbons to demonstrate the unique and unexpected non-toxic properties of monobrominated acyclic perfluorocarbons.

The following brominated perfluorocarbons were used:

| Code | Formula | Chemical Class |
|------|---------|----------------|
| A | $CF_3(CF_2)_6CF_2Br$ | monobromo, acyclic |
| B | $CF_3(CF_2)_3CF_2Br$ | monobromo, acyclic |
| C | $Br(CF_2)_4Br$ | dibromo, acyclic |
| D | $Br(CF_2)_2Br$ | dibromo, acyclic |
| E | 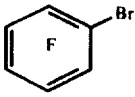 | monobromo, cyclic |
| F | 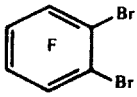 | dibromo, cyclic |
| G | $CF_3CFBrCF_2Br$ | dibromo, acyclic |

The above brominated perfluorocarbons were orally administered to both anesthetized and non-anesthetized rats at controlled dosages ranging from 4 ml./kg to 64 ml/kg. Mortality rates were determined and observations of physical activity were closely followed. The results indicated that the order of toxicity (as measured by mortality rate) is A<B<C<D<E<F<G. Only the monobromo-acyclic compounds of the present invention (codes A and B) did not produce diarrhea. On the other hand, dibromo compounds (codes C, D, F, and G) as well as the monobromo-cyclic compound (code E) which had higher mortality rates also produced diarrhea. Code A was preferred over code B for applications (e.g., in the lungs) where a radiopaque agent is likely to become confined and vaporize before it can be eliminated or excreted, since code B was found to vaporize at a vapor pressure below that of code A.

The results of the above studies were confirmed by other toxicity studies with different species of animals, including guinea pigs, dogs, rabbits and hamsters as well as with emulsified forms of the brominated perfluorocarbons. Multiple oral administration studies further confirmed the above results, and indicated there was no accumulation of radiopaque agent in the bodies of animals administered the monobrominated acyclic perfluorocarbons.

EXAMPLE III

In this example other than oral administration procedures were used. Rectal administration studies involving rats and dogs subjected to the radiopaque agents of the present invention indicated no apparent ill-effects.

Intraperitoneal and subcutaneous administration studies, conducted primarily to determine the effect of leakage of the radiopaque agent into the peritoneal cavity or the subcutaneous tissue during either oral or rectal administration, indicated that the radiopaque agents of the present invention produce minimal inflammatory reaction and no evidence of oncogenesis.

EXAMPLE IV

In this example, perfluoroctylbromide proved unexpectedly superior to "Dionosil" and barium sulfate when introduced into the tracheobronchial trees of rats, rabbits, dogs and pigs. When used as the pure liquid, perfluoroctylbromide did not produce coughing and resulted in minimal inflammatory reaction. Moreover, the liquid perfluoroctylbromide flowed readily into the alveolar sacs and small respiratory passages resulting in X-ray visualization of this portion of the lungs. This property is useful in outlining emphysematous areas of the lung, cavitations and consolidation.

When "Dionosil" was used, there was coughing. The material did not flow into alveolar sacs readily but stayed in the trachea and bronchi, and, there was a significant inflammatory reaction.

When barium sulfate was used, there was coughing and respiratory distress and a high mortality rate. The barium sulfate did not flow readily into the alveolar sacs and also caused inflammatory reaction.

The perfluoroctylbromide had high oxygen solubility and oxygen diffusion properties as illustrated by the observation that a hamster could be completely submerged or drowned in ventilated perfluoroctylbromide for 10 minutes with long term survival.

EXAMPLE V

In this example, emulsions of perfluoroctylbromide were found to outline the tracheobronchial tree with little or no passage into the alveolar sacs.

The emulsions were prepared by slowly mixing, by hand stirring, about 10 parts by weight perfluoroctylbromide with about 1 part by weight lactated Ringer's Solution which contained a very small amount of an emulsifying agent ("Pluronic F-68"), a condensate of ethylene oxide with a hydrophobic base formed by condensing propylene oxide with propylene glycol.

These emulsions of perfluoroctylbromide were superior to "Dionosil" and barium sulfate in that there was very little irritation of the tracheobronchial tree and little impairment in ventilization and gas exchange. The emulsions of perfluoroctylbromide were also superior in that they were cleared by the mucociliary mechanisms and vaporization.

EXAMPLE VI

In this example, radiopaque emulsions of the present invention were administered intravenously to rabbits, dogs, and rats, and resulted in visualization of the blood vessels. Injection of the liquid form is to be avoided because of the toxic results, as evidenced by rapid mortality. In appropriate doses, the radiopaque agents of the present invention, when in emulsion form, were satisfactory for radiopacification of very small blood vessels. In the process, a unique and unexpected radiopacification of the spleen was accomplished. The perfluoroctylbromide was phagocytosed by the reticuloendothelial cells of the spleen. The spleen thus became clearly visible with X-rays within 30 minutes after injection of the emulsion of perfluoroctylbromide. The radiopacification of the spleen diminished gradually over the next few months. The unexpected observation of radiopacification of the spleen may be useful in defining injuries and tumors of the spleen by X-ray, in locating ectopic splenic tissue an in monitoring the activity of the reticuloendothelial system of the spleen in certain disease states. The liver was also faintly opacified due to phagacytosis of the perfluoroctylbromide by the reticuloendothelial cells of the liver when the splenic cells were saturated.

While the present invention has been described with reference to the above examples, it is not to be limited thereto. Modifications within its spirit and scope will be apparent to those skilled in the art.

What is claimed is:

1. In a process for radiologically examining a part of the body of an animal, the improvement comprising contacting said body part with an effective amount of a radiopaque agent comprising a non-toxic monobrominated acyclic perfluorocarbon.

2. The process of claim 1 wherein said radiopaque agent comprises a perfluoroalkyl bromide having 6 to 8 carbon atoms in the molecule.

3. The process of claim 1 wherein said radiopaque agent is $CF_3(CF_2)_6CF_2Br$.

4. The process of claim 1 wherein said radiopaque agent is administered in the form of an aqueous emulsion.

5. The process of claim 1 wherein said radiopaque agent is administered in the form of an aerosol.

6. The process of claim 1 wherein said body part is the spleen.

7. The process of claim 1 wherein said body part is the gastrointestinal tract.

8. The process of claim 1 wherein said body part is the tracheobronchial tree and the lungs.

9. A non-toxic radiopaque emulsion consisting essentially of an aqueous phase, an effective amount of a monobrominated acyclic perfluorocarbon and a minor amount of an emulsifying agent.

10. The emulsion of claim 9 wherein said perfluorocarbon is a perfluoroalkyl bromide having 6–8 carbon atoms in the molecule.

11. The emulsion of claim 10 wherein said perfluorocarbon is $CF_3(CF_2)_6CF_2Br$.

12. The emulsion of claim 9 wherein said perfluorocarbon is present in a concentration in the range from about 1 to about 12 parts by weight for each part by weight of aqueous phase.

13. The emulsion of claim 9 wherein said aqueous phase comprises lactated Ringer's Solution.

* * * * *